(12) United States Patent
Zhang et al.

(10) Patent No.: US 7,208,965 B2
(45) Date of Patent: Apr. 24, 2007

(54) PLANAR VIEW TEM SAMPLE PREPARATION FROM CIRCUIT LAYER STRUCTURES

(75) Inventors: Wen Yi Zhang, Singapore (SG); Siew Khim Oh, Singapore (SG)

(73) Assignee: Systems on Silicon Manufacturing Co. Pte. Ltd., Singapore (SG)

( * ) Notice: Subject to any disclaimer, the term of this patent is extended or adjusted under 35 U.S.C. 154(b) by 6 days.

(21) Appl. No.: 11/022,325

(22) Filed: Dec. 23, 2004

(65) Prior Publication Data

US 2006/0139049 A1    Jun. 29, 2006

(51) Int. Cl.
*G01R 31/02* (2006.01)

(52) U.S. Cl. ............... 324/754; 324/158.1; 250/492.3; 438/463

(58) Field of Classification Search ............... None
See application file for complete search history.

(56) References Cited

U.S. PATENT DOCUMENTS 6,188,068 B1 * 2/2001 Shaapur et al. ............. 250/307
6,194,720 B1 * 2/2001 Li et al. ...................... 250/311
6,362,475 B1 * 3/2002 Bindell et al. ............... 250/307
6,420,722 B2 * 7/2002 Moore et al. ............ 250/559.27

* cited by examiner

*Primary Examiner*—Minh N. Tang
(74) *Attorney, Agent, or Firm*—Christie, Parker & Hale, LLP

(57) ABSTRACT

A method of preparing a planar view TEM sample of a planar portion of a circuit layer structure formed on a substrate. The method includes polishing the substrate circuit layer structure until a cross-sectional polishing face has substantially reached a first side face of the planar portion of the circuit layer structure; forming a trench structure in the cross-sectional polishing face. The trench structure extends into the cross-sectional polishing face substantially in the direction parallel to the substrate such that top and bottom faces of the planar portion of the circuit layer structure are exposed, wherein the planar portion of the circuit layer structure extends substantially parallel to the substrate from the first side face. The method further includes performing a cut around the first side face to free the planar portion of the circuit layer structure.

10 Claims, 8 Drawing Sheets

PLANAR VIEW TEM SAMPLE PREPARATION FROM CIRCUIT LAYER STRUCTURES

FIELD OF INVENTION

The present invention relates broadly to a method of preparing a planar view TEM sample of a planar portion of a circuit layer structure.

BACKGROUND

In circuit failure analysis, such as Ultra-Large Scale Integration (ULSI) circuit failure analysis, Transmission Electron Microscopes (TEMs) are typical tools that may be used. For preparation of TEM samples, the circuits for testing have to undergo preparation and localisation procedures. The circuits typically comprise multi-layered structures on a wafer substrate.

TEM samples are typically prepared so that they may be viewed in either cross-sectional or planar-view orientations (where the orientations are with respect to the circuits).

For planar-view TEM samples, the circuits on wafers are typically first mechanically polished and lapped from the back surface of the wafers to an extent that the layer in which the area to be viewed is almost reached. Typically, the thickness of the relevant remaining circuits are about 50 μm. Dimpling is then typically performed to obtain a final thickness of the relevant remaining circuits of about 5 μm. Ion milling (for example, Ar+ milling) is then typically carried out on the remaining circuits such that the specific area is located in a wedge-like region around a crater or hole milled. This region is then used for TEM imaging.

The above approach is time-consuming and may result in mechanical damage to the TEM sample. Furthermore, typically, it is difficult to determine if the area being ion milled is the correct area, ie. there are limited visual aids available in current planar-view TEM sample preparation techniques.

For cross-sectional view TEM samples, localization of specific areas for TEM analysis is typically achieved with the use of a Scanning Electron Microscope (SEM) in a dual beam Focused Ion Beam (FIB) system. As illustrated in FIG. 1, the SEM beam column (102) and a tilted FIB column (104) are calibrated and adjusted to "coincide" on a sample at a "coincidental" point (106). Using this technique, the specific area to be localised may be marked out by the SEM beam column (102) while the actual milling of the area may be conducted with the FIB column (104).

With reference to FIG. 2 (a), a typical circuit (202) comprising multi-layered structures is disposed on a substrate (204). A site of interest (206) to be imaged in cross-sectional view by the TEM is being prepared for imaging. Two trenches, for example, (208) and (210), are ion milled on either side of the site of interest (206). It has to be noted that although ion milling with the substrate in a planar orientation, the area to be viewed on the prepared site of interest (206) is a cross-sectional area (212) of the site of interest (206).

With reference to FIG. 2 (b), the TEM sample preparation process in FIG. 2 (a) is illustrated in another perspective view. As noted above, trenches, (208) and (210), have been ion-milled on either side of the site of interest (206). The site of interest is then "cut-out" via typical U-shaped ion milling cut (213) and lifted using an electrostatic probe (not shown). It is noted that the final TEM sample (214) obtained is a cross-sectional portion of circuit (202). Therefore, typical planar ion-milling techniques yield cross-sectional TEM samples.

Often, a planar-view TEM sample may be desired over a cross-sectional view, due to the larger field of view offered by the former. However, as will be appreciated, current FIB/SEM techniques are not suitable for preparation of planar-view TEM samples.

SUMMARY

In accordance with a first aspect of the present invention there is provided a method of preparing a planar view TEM sample of a planar portion of a circuit layer structure, the method comprising polishing the circuit layer structure until a cross-sectional polishing face of the circuit structure has substantially reached a first side face of the planar portion forming a trench structure in the cross-sectional polishing face such that top and bottom faces of the planar portion are exposed; and performing a cut along the top and bottom faces of the planar region to free the planar view TEM sample.

The circuit layer structure may be mounted onto a sample holder prior to the polishing of the circuit layer structure, and remains mounted on said same sample holder during the forming of the trench structure and the performing of the cut.

The forming of the trench may comprise ion milling.

The ion milling may comprise utilising a focused ion beam (FIB).

The polishing of the circuit layer structure may comprise a mechanical polishing.

The method may further comprise utilising a scanning electron microscope for imaging the cross-sectional polishing face during forming of the trench structure.

The method may further comprise utilising a laser marker to mark out an approximate location of the planar region during manipulation of the circuit layer structure for forming the trench structure.

The method may further comprise depositing a protective layer on the cross-sectional polishing face substantially in an area of the first side face of the planar region, prior to forming the trench structure.

The method may further comprise fine milling of the planar view TEM sample prior to extracting the planar view TEM sample from the circuit layer structure.

The method may further comprise fine polishing of the planar view TEM sample prior to extracting the planar view TEM sample from the circuit layer structure.

BRIEF DESCRIPTION OF THE DRAWINGS

Embodiments of the invention will be better understood and readily apparent to one of ordinary skill in the art from the following written description, by way of example only, and in conjunction with the drawings, in which:

FIG. 2 (b) is a perspective illustration of a typical sample preparation as illustrated in FIG. 2 (a).

DETAILED DESCRIPTION

In an example embodiment, a TEM sample may be prepared in a planar-view orientation such that a large field of view may be obtained for TEM imaging.

Figure 3:
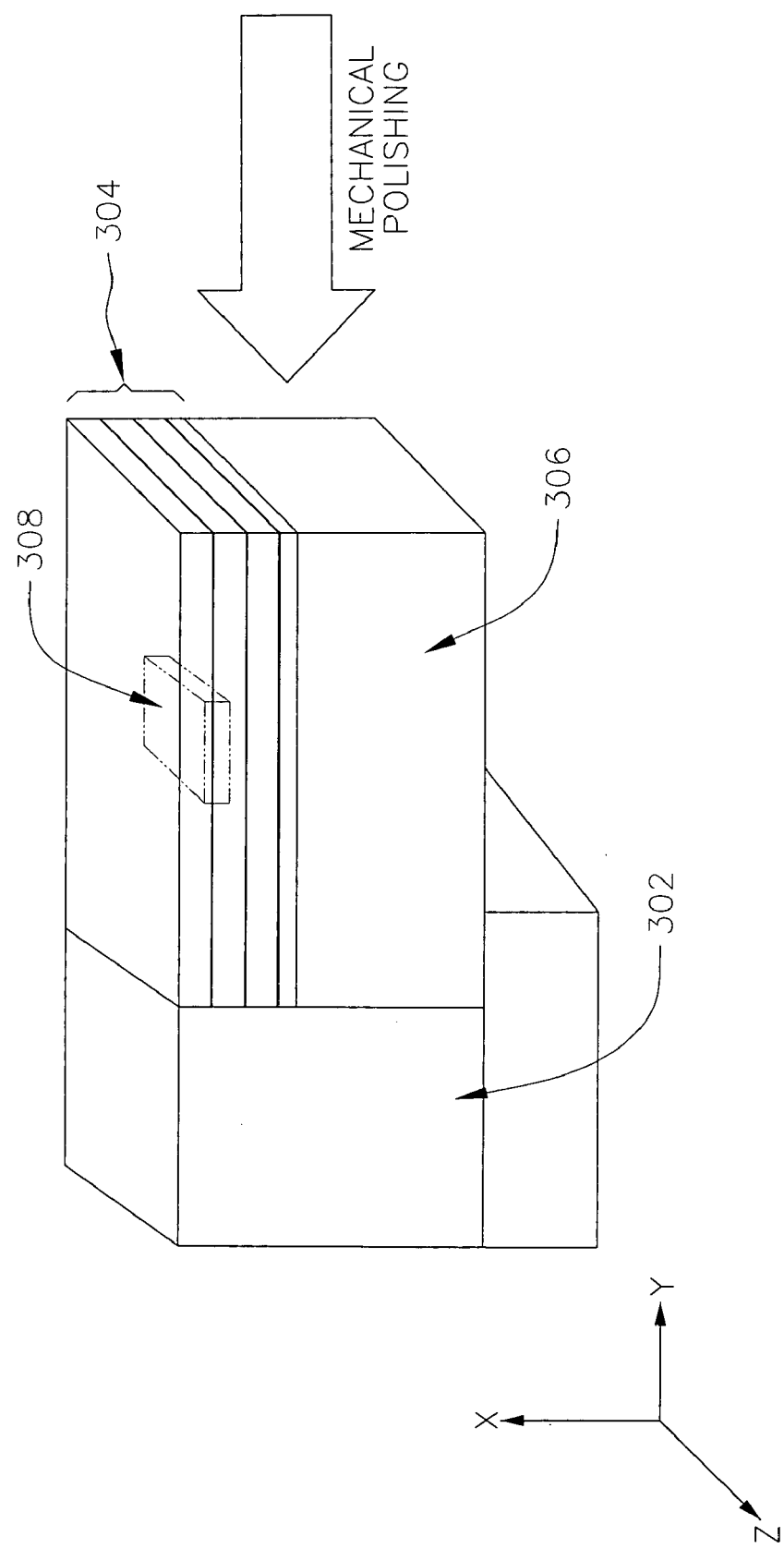
FIG. 3 is an illustration of mechanical polishing process during a TEM sample preparation in an example embodiment.

In the example embodiment, as illustrated in FIG. 3, a holder (302) is used to secure and keep in place circuit layers, for example (304), disposed on a substrate (306). The substrate (306) may be mounted on the holder (302) by way of a retaining material layer deposited around and above one end of the substrate (306) and a surface of the holder (302). Mechanical polishing is then carried out in a cross-sectional direction with respect to the circuit layers (304), as indicated in FIG. 3. Mechanical polishing is carried out until the site of interest (308) in the circuit layers (304) is almost reached.

Figure 4:
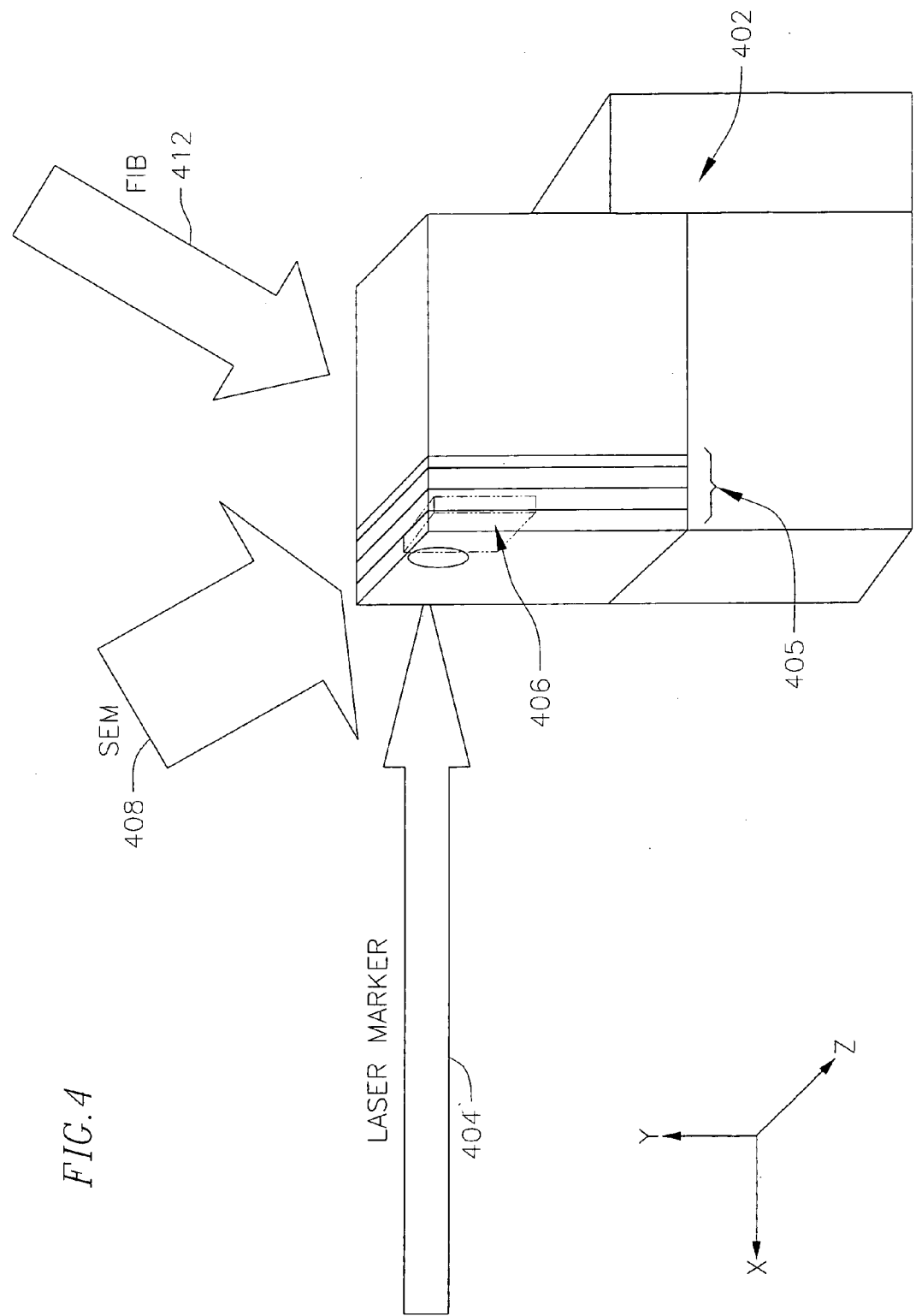
FIG. 4 is a schematic diagram of a setup for SEM-assisted FIB milling of circuit layers during a TEM sample preparation in an example embodiment.

With reference to FIG. 4, after mechanical polishing, in the example embodiment, the holder (402) is secured where FIB/SEM techniques may be utilised for TEM sample preparation. In the example embodiment, a laser marker (404) may be used to mark out the approximate location of the site of interest (406) in the circuit layers (405). The SEM (408) can be utilised as an additional visual tool to view the site of interest (406) within the circuit layers (405).

Figure 1:
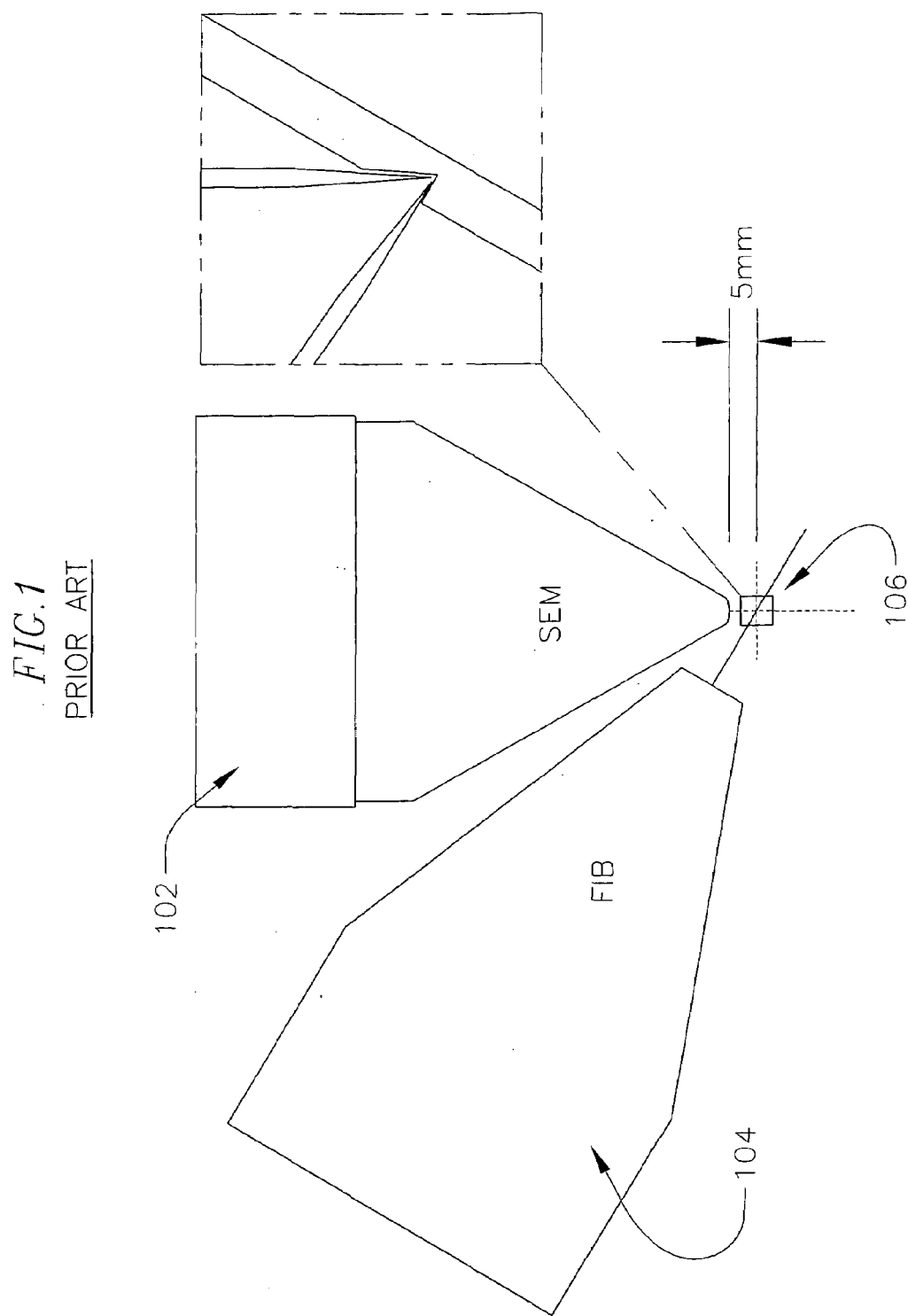
FIG. 1 is an illustration of a typical configuration of dual beam Focused Ion Beam (FIB) system.
Figure 2:
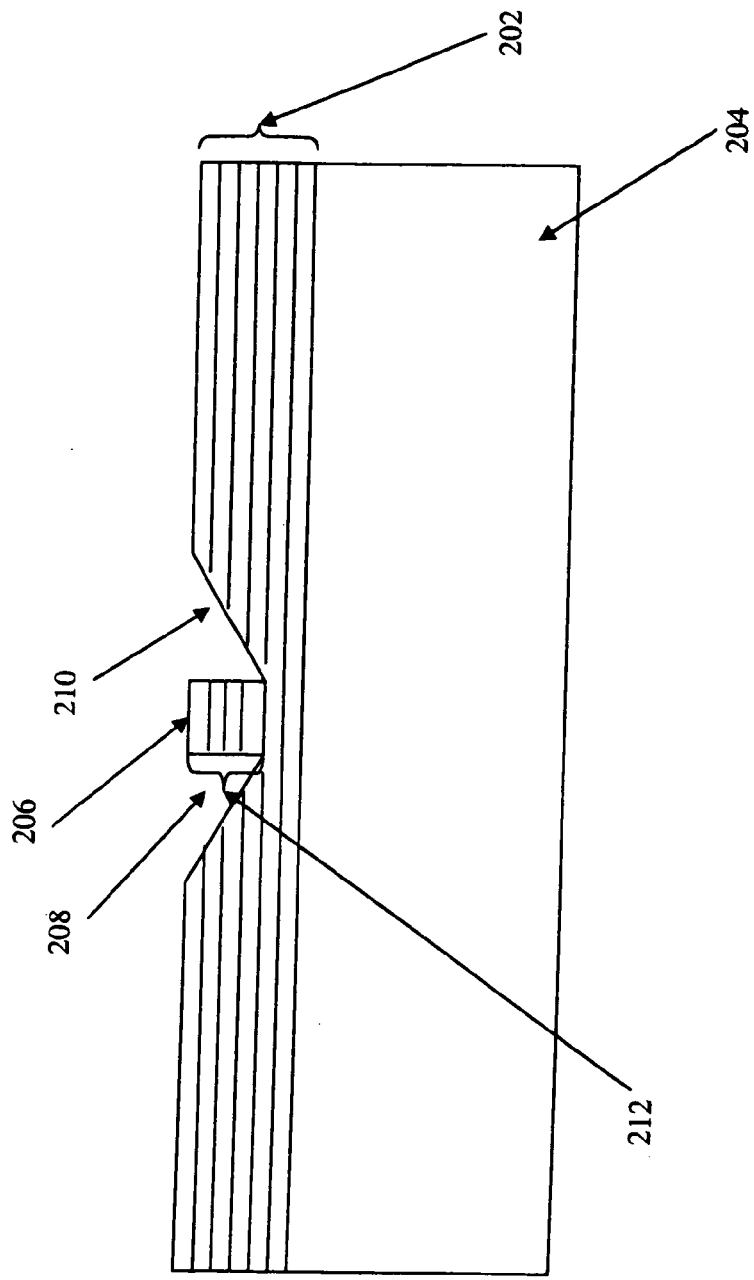
FIG. 2 (a) is an illustration of a typical sample preparation with ion-milling of two trenches on each side of a site of interest on a planar surface.
Figure 2:
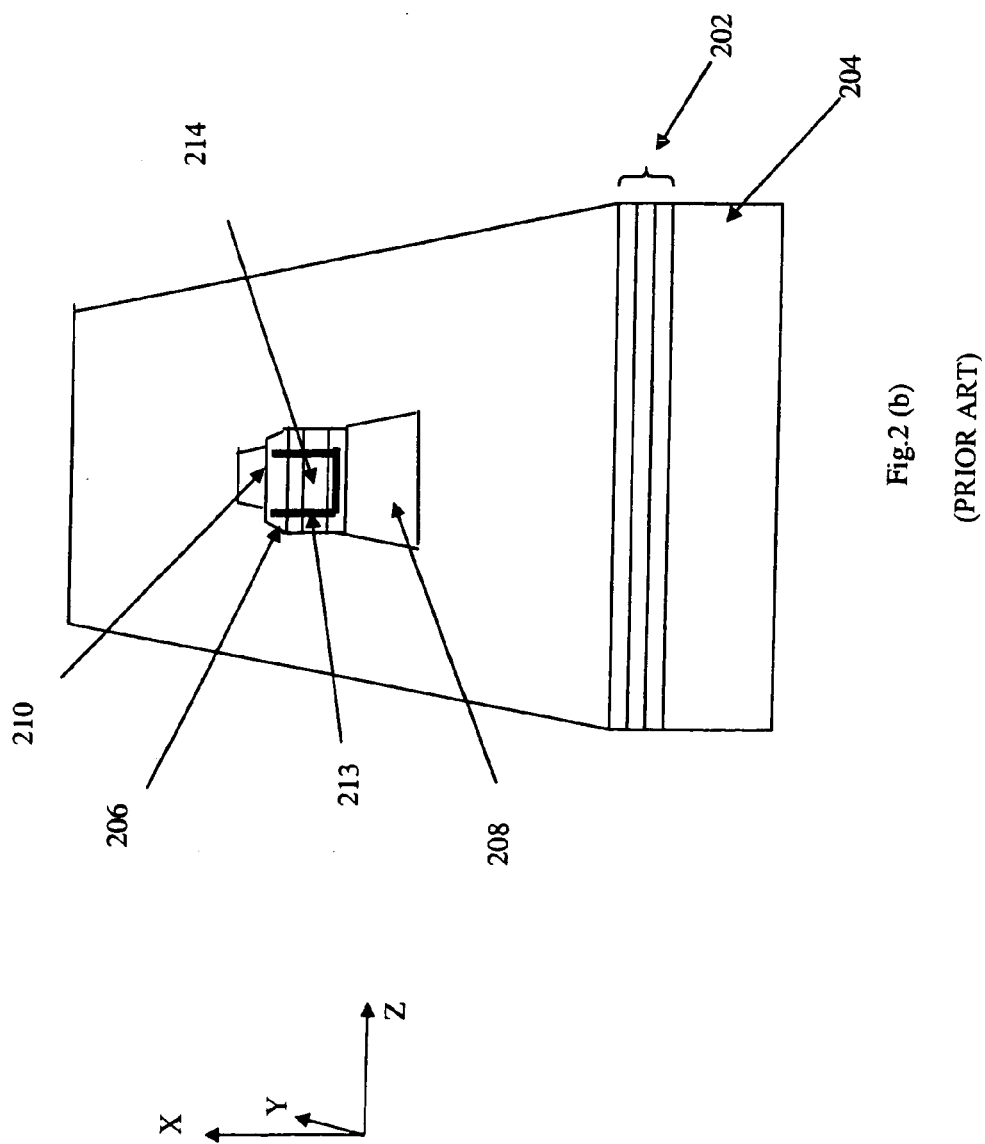
Figure 5:
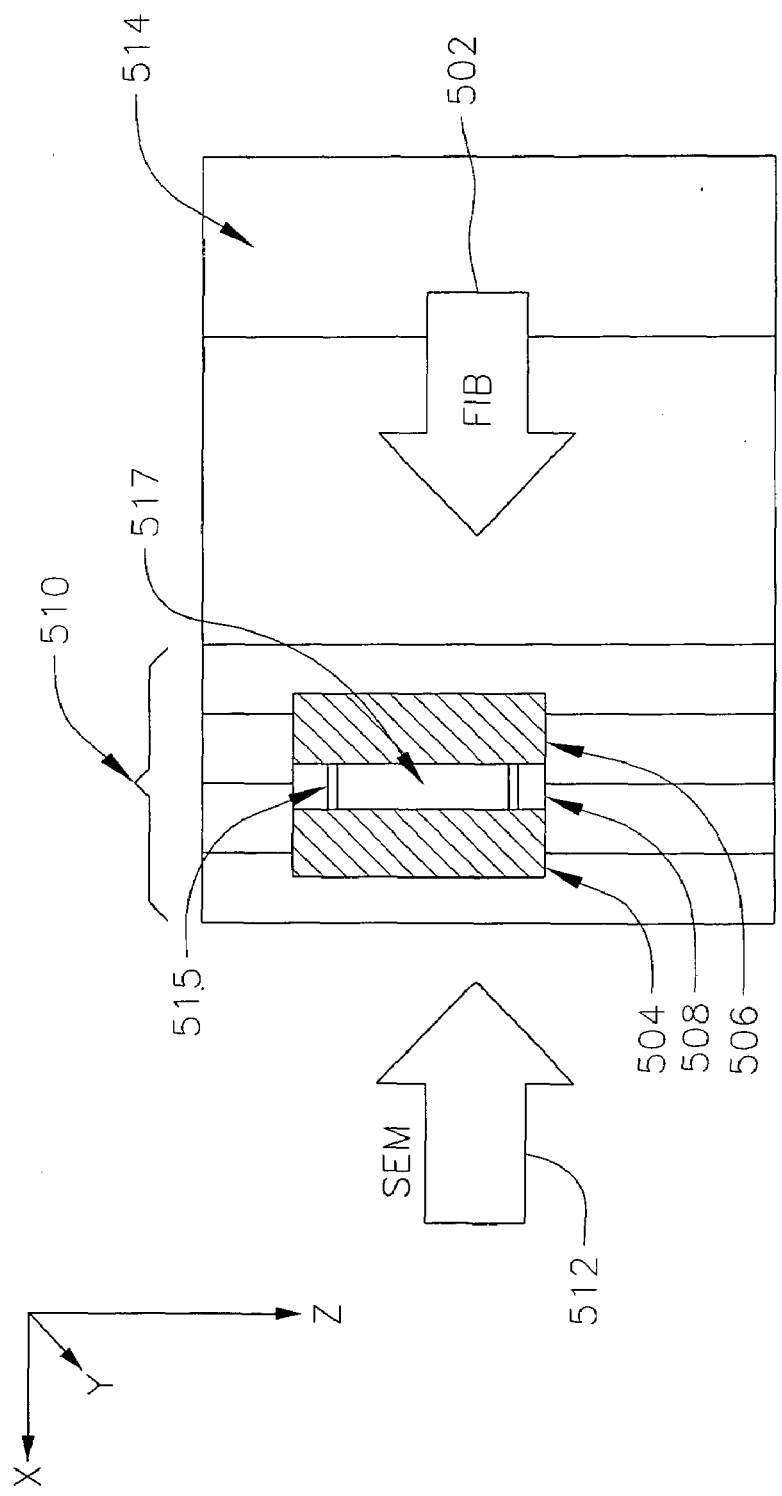
FIG. 5 is an illustration of SEM-assisted FIB milling of circuit layers during a TEM planar-view sample preparation in an example embodiment.

With reference to FIG. 5, in the example embodiment, the FIB (502) is utilised to mill two trenches, for example (504) and (506), on each side of the site of interest (508) on the circuit layers (510). A protective film (not shown) may first be deposited over the site of interest (508). The depth of the trenches, (504) and (506), can be determined based on the depth of the site of interest (508) within the circuit layers (510). The depth of the site of interest (508) within the circuit layers (510) may be visualised by the SEM (512). After the milling of the two trenches, (504) and (506), the holder (514) is tilted so that U-shaped FIB-milling, as indicated at numeral (515), of the site of interest (508) is performed to cut free a TEM sample (517) (compare FIG. 2(b)).

Subsequently, in the example embodiment, the "free" TEM sample (517) may undergo fine polishing and fine milling. This process may thin the TEM sample (517) to be electron-transparent where it will then be suitable for TEM imaging. The resulting TEM sample (517) after processing may then be extracted by an electrostatic probe (not shown) for TEM imaging.

Figure 6:
FIG. 6 is an illustration of a field of view of a sample prepared in a planar-view orientation in an example embodiment.

By preparing a TEM sample (600) in the planar view orientation as illustrated in FIG. 6, the area exposed is larger as compared to typical cross-sectional view orientation of sample preparation. This attribute allows efficient analysis of the sample by the TEM as a larger area is exposed by preparing planar view TEM samples.

The benefits of the example embodiments may include enabling planar-view sample preparation. This is useful as a large field of view of the specific area may be inspected during root cause analysis. This may improve typical TEM sample preparation methods being used in institutions and industries as well. In addition, the method of preparation in the example embodiments also offers a number of advantages over typical planar-view orientation sample preparations. Besides offering a visualisation of the site of interest during preparation, the example embodiments may offer savings in time and effort through the combination of polishing and FIB-milling as compared to typical preparation processes.

Furthermore, in the example embodiment described, the substrate (with circuit layers) is mounted on the same holder during the various TEM sample preparation processes. More particularly, the same holder is used during the mechanical polishing and the ion milling processing. Compared with previous planar view TEM sample preparation techniques, which require different sample holders during the processing, this can provide a number of advantages, including a time saving and a reduced risk of damage to the sample as a result of re-mounting of the sample.

Figure 7:
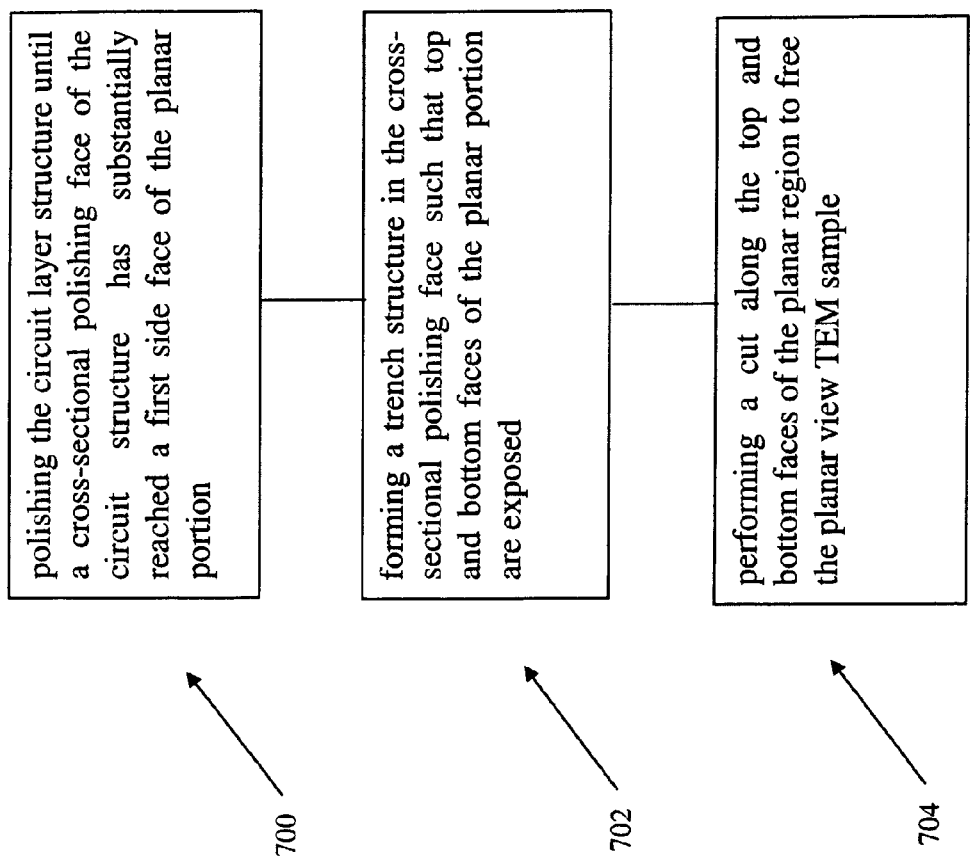
FIG. 7 shows a flow-chart illustrating a method of preparing a planar view TEM sample of a planar portion of a circuit layer structure according to an example embodiment.

FIG. 7 shows a flow-chart illustrating a method of preparing a planar view TEM sample of a planar portion of a circuit layer structure according to an example embodiment. At step (700), the circuit layer structure is polished until a cross-sectional polishing face of the circuit structure has substantially reached a first side face of the planar portion. At step (702), a trench structure is formed in the cross-sectional polishing face such that top and bottom faces of the planar portion are exposed. At step (704), a cut is performed along the top and bottom faces of the planar region to free the planar view TEM sample.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A method of preparing a planar view TEM sample of a planar portion of a circuit layer structure formed on a substrate, the method comprising
    polishing the substrate in a direction parallel to the substrate until a cross-sectional polishing face has substantially reached a first side face of the planar portion of the circuit layer structure;
    forming a trench structure in the cross-sectional polishing face, the trench structure extending into the cross-sectional polishing face substantially in the direction parallel to the substrate such that top and bottom faces of the planar portion of the circuit layer structure are exposed, wherein the planar portion of the circuit layer structure extends substantially parallel to the substrate from said first side face; and
    performing a cut around said first side face to free the planar portion of the circuit layer structure.

2. The method as claimed in claim 1, wherein the substrate is mounted onto a sample holder prior to the polishing of the substrate, and remains mounted on said same sample holder during the forming of the trench structure and the performing of the cut.

3. The method as claimed in claim 1, wherein one or more of the forming of the trench, and the performing of the cut, comprises ion milling.

4. The method as claimed in claim 3, wherein the ion milling comprises utilizing a focused ion beam (FIB).

5. The method as claimed in claim 1, wherein the polishing of the substrate comprises a mechanical polishing.

6. The method as claimed claim 1, further comprising utilizing a scanning electron microscope for imaging the cross-sectional polishing face during forming of the trench structure.

7. The method as claimed in claim 1, further comprising utilizing a laser marker to mark out an approximate location of the planar region during manipulation of the substrate for forming the trench structure.

8. The method as claimed claim 1, further comprising depositing a protective layer on the cross-sectional polishing face substantially in an area of the first side face of the planar portion of the circuit layer, prior to forming the trench structure.

9. The method as claimed in claim 1, further comprising fine milling of the planar portion of the circuit layer structure prior to extracting the planar portion of the circuit layer structure from the circuit layer structure.

10. The method as claimed in claim 1, further comprising fine polishing of the planar portion of the circuit layer structure prior to extracting the planar portion of the circuit layer structure from the circuit layer structure.

* * * * *